(12) United States Patent
Wiseman

(10) Patent No.: US 6,989,529 B2
(45) Date of Patent: Jan. 24, 2006

(54) PLASMA TORCH

(75) Inventor: Alan G. Wiseman, Wheelers Hill (AU)

(73) Assignee: Varian Australia PTY Ltd., Mulgrave (AU)

( * ) Notice: Subject to any disclaimer, the term of this patent is extended or adjusted under 35 U.S.C. 154(b) by 74 days.

(21) Appl. No.: 10/482,243

(22) PCT Filed: Mar. 28, 2002

(86) PCT No.: PCT/AU02/00386

§ 371 (c)(1),
(2), (4) Date: Dec. 19, 2003

(87) PCT Pub. No.: WO03/005780

PCT Pub. Date: Jan. 16, 2003

(65) Prior Publication Data

US 2004/0183008 A1    Sep. 23, 2004

(30) Foreign Application Priority Data

Jul. 3, 2001 (AU) .................................. PR 6099
Jul. 12, 2001 (AU) .................................. PR 6347

(51) Int. Cl.
*G01N 21/73* (2006.01)

(52) U.S. Cl. ........................................ 250/288; 356/316
(58) Field of Classification Search ................ 250/288
See application file for complete search history.

(56) References Cited

U.S. PATENT DOCUMENTS 5,818,581 A * 10/1998 Kurosawa et al. .......... 356/316

* cited by examiner

*Primary Examiner*—John R. Lee
*Assistant Examiner*—Paul M. Gurzo
(74) *Attorney, Agent, or Firm*—Bella Fishman; Edward H. Berkowitz

(57) ABSTRACT

A torch for producing an inductively coupled or microwave induced plasma for use in spectrochemical analysis. The torch includes a central tube (25) for conveying a flow of a gas carrying sample aerosol to a plasma (17) produced in the torch. The tube (25) has an inlet (31) and an outlet (39) of smaller size than the inlet and is shaped to deliver a substantially laminar flow of the gas at the outlet (39). The tube (25) is tapered along at least a substantial portion of its length such that its cross-section area gradually and smoothly reduces towards its outlet (39) along at least a substantial portion of its length. It has been found that such a tapered tube is resistant to obstruction by salts deposited from samples containing high levels of dissolved solids.

8 Claims, 4 Drawing Sheets

Figure 1:
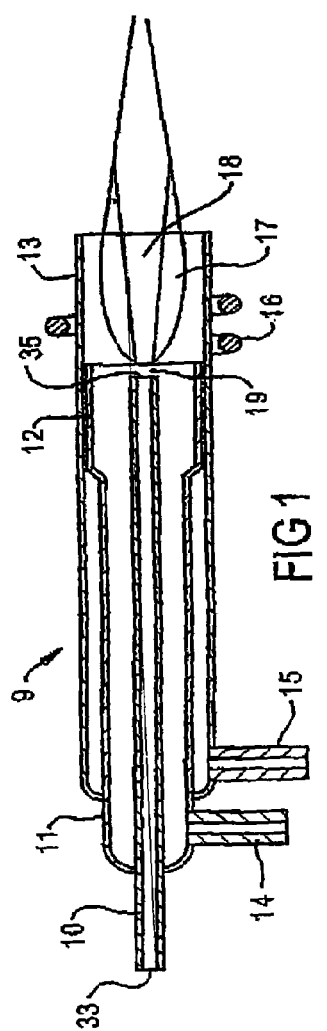

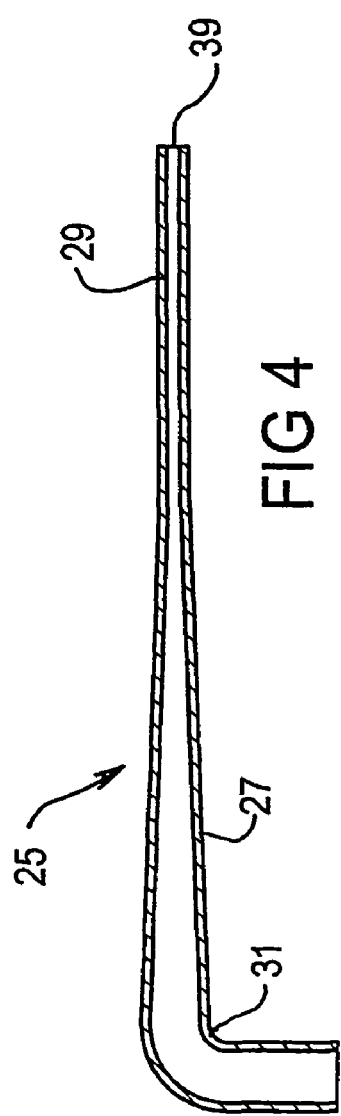
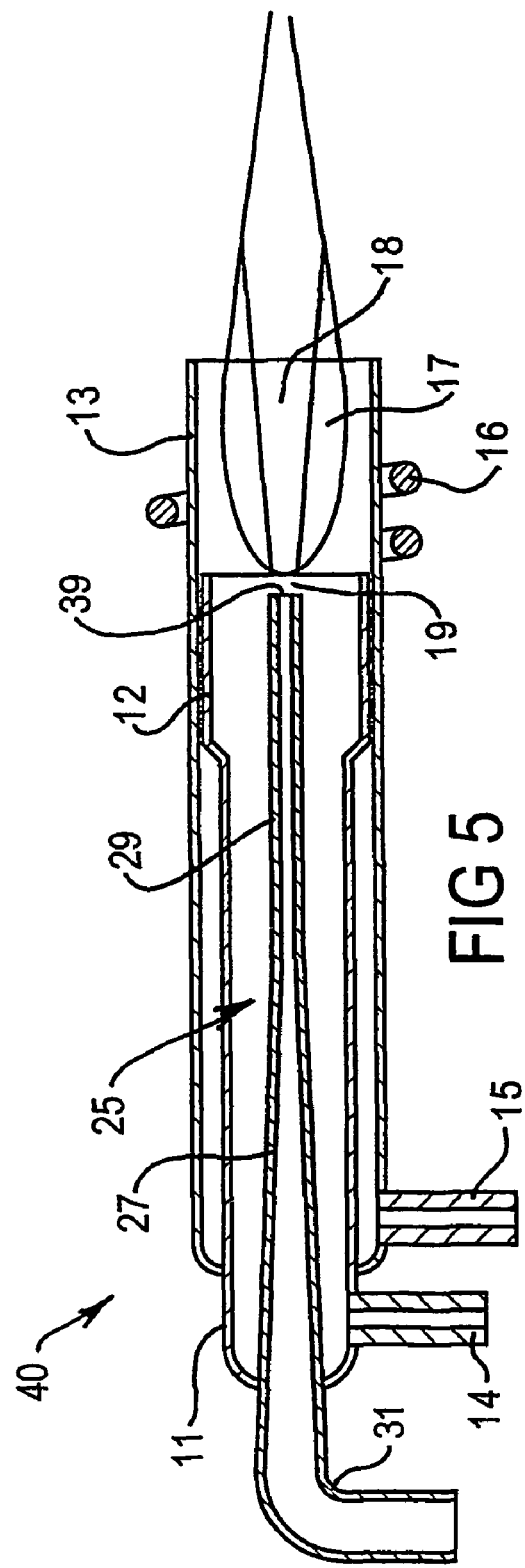

PLASMA TORCH

TECHNICAL FIELD

This invention relates to a plasma torch for spectrochemical analysis, for example for producing an inductively coupled plasma or a microwave induced plasma.

BACKGROUND OF THE INVENTION

A common requirement in spectrochemical analysis with inductively coupled or microwave induced plasma torches is to analyse liquid samples having relatively high concentrations of dissolved solids. In extreme cases the concentrations of such samples might approach the saturation point of one of the dissolved components. Liquid samples are usually introduced a plasma torch as aerosols produced by a nebulizer. Attempts to analyse highly concentrated samples can result in salts coming out of solution as the nebulised aerosol is generated and as it is transported through the torch. Salt particles are often deposited in the nebulizer or in the torch, ultimately causing blockages that require the analysis to be stopped and the apparatus to be disassembled and cleaned. This wastes valuable time. Nebulisers that are resistant to obstruction by salts are known in the art, but obstruction of the plasma torch has continued to cause difficulty.

An object of the present invention is to provide a torch for producing a plasma for use in spectrochemical analysis that is resistant to obstruction by salts deposited from samples containing high levels of dissolved solids.

SUMMARY OF THE INVENTION

The invention provides a torch for producing a plasma for use in spectrochemical analysis including a tube for conveying a flow of a gas carrying sample aerosol to a plasma produced in the torch by an electromagnetic field, the tube having an inlet and an outlet of smaller size than the inlet, and being shaped to deliver a substantially laminar flow of the gas at the outlet, wherein the tube is tapered along at least a substantial portion of its length such that its cross-sectional area gradually and smoothly reduces towards its outlet along said at least a substantial portion of its length.

As the aerosol travels from the inlet of the tube of the torch (typically 4 to 8 mm ID) to the outlet of the tube (typically 0.8–3 mm ID) the velocity of the aerosol increases. This change in velocity (and associated changes in pressure) ought to occur as smoothly as possible, such that turbulence and pressure changes are minimized. The invention meets the stated object by providing a gradual reduction in cross-sectional area between the inlet and the outlet and by providing a smooth transition between the said tapered portion and any parallel portions at each end. The taper may be constant (that is, linear), exponential or of any other shape that can provide an appropriately smooth pathway of decreasing cross-sectional area, blending smoothly into any parallel portions. Such a shape is produced naturally when glass or quartz tube is heated and stretched to produce the taper. If the tube were to be manufactured from ceramic material (either by machining and sintering or moulding), or by shrinking quartz onto a mandrel, care would need to be taken in machining, or in the design and construction of the mould or mandrel, to avoid sharp or abrupt transitions between the tapered portion and any adjacent parallel portions. The length of the tapered portion may be at least five times the internal diameter of the inlet of the tube and is advantageously from five to ten times the internal diameter of the inlet of the tube. Such a design eliminates relatively sudden transitions in the cross sectional area of the tube of the plasma torch, as have been provided in prior art torches, at which salts are preferentially prone to deposit.

Any turbulence and changes in pressure that may be associated with the transition between a parallel portion of tube at the outlet end and the said tapered portion should occur at a location sufficiently remote from the plasma to be largely unaffected by the heat radiated from the plasma or conducted down the tube from the plasma. This can be achieved in the invention by ensuring that the final change in internal diameter occurs at a distance of 40 to 50 mm from the outlet end of the tube. The known relatively sudden transition in cross-sectional area of a tube in a prior art torch is typically located near the outlet end of the tube and is thus nearby the heat of the plasma. The invention reduces the influence of this factor given the tapered portion provides a gradual and smooth transition between the inlet and outlet cross sections and also that it may be located as remotely as possible from the heat of the plasma, for example, the tapered portion may commence at the inlet.

For a better understanding of the invention and to show how it may be carried into effect, preferred embodiments thereof will now be described, by way of non-limiting example, with reference to the accompanying drawings.

BRIEF DESCRIPTION OF THE DRAWINGS

FIG. 1 schematically shows a typical prior art inductively coupled plasma torch.

FIG. 2 illustrates a known modification for a tube of the torch of FIG. 1 for conveying a flow of a gas carrying sample aerosol.

FIG. 3 illustrates an embodiment of a tube for conveying a flow of a gas carrying sample aerosol for a torch according to the invention.

FIG. 4 illustrates a second embodiment of a tube for a torch according to the invention.

FIG. 5 schematically shows a torch according to an embodiment of the invention.

FIG. 6 is a graph illustrating spectrochemical analysis results from a plasma sustained by a plasma torch according to an embodiment of the invention.

FIG. 7 is a graph illustrating performance of a plasma torch according to an embodiment of the invention in comparison to a prior art plasma torch.

DETAILED DESCRIPTION

A typical inductively coupled plasma torch 9 is shown in FIG. 1. It consists of three concentric tubes, 10, 11 and 13, usually made out of fused quartz. FIG. 1 shows a torch 9 in which the three tubes are permanently fused together, but it is known in the art to provide a mechanical arrangement whereby the three tubes 10, 11 and 13 are held in their required positions and wherein one or more of the tubes 10, 11 and 13 can be removed and replaced. Such an arrangement is called a demountable torch.

Tube 13 is the outermost of the three tubes. Tube 11 is the intermediate tube and may be provided with a portion 12 of larger diameter, which may in some designs extend over the entire length of tube 11. The purpose of portion 12 is to provide a narrow annular gap between tubes 11 and 13 for the passage of a plasma forming gas (typically argon) that is supplied though a gas inlet 15. The narrow gap imparts a desirably high velocity to the gas. Radiofrequency induction coil 16 is supplied with radiofrequency current from a power supply (not shown). Plasma 17 is initiated by momentarily applying a high-voltage spark (by means known in the art and not shown) to the gas entering through gas inlet 15. Plasma 17 is sustained by inductive coupling of the radiofrequency electromagnetic field generated by coil 16 with plasma 17, as is known in the art. A small flow of gas is supplied to tube 11-12 through gas inlet 14. This serves to keep plasma 17 at an appropriate distance from the nearby ends 19 of tubes 11–12 and 10, so that the ends 19 of tubes 11-12 and 10 do not overheat.

For a microwave induced plasma instead of an inductively coupled plasma, the coil 16 would not be present and the torch 9 would be suitably associated with means for applying a microwave electromagnetic field to the torch 9, for example the torch 9 may be appropriately located through a resonant cavity to which the microwave energy is supplied.

A flow of gas carrying sample aerosol (not shown) for analysis is introduced by known means (not shown) into the end of tube 10 remote from the plasma (i.e. the tube's inlet 33). The aerosol-laden gas emerges from the other end (i.e. the outlet 35) of tube 10 adjacent to plasma 17 with sufficient velocity to pass through plasma 17. The passage through plasma 17 of gas and aerosol emerging from tube 10 forms a central channel 18 in plasma 17. Aerosol droplets passing from the outlet 35 of tube 10 into central channel 18 are progressively dried, melted, and vaporised by the heat of plasma 17. The vaporised sample is subsequently converted to atoms and ions by the heat of plasma 17, and these atoms and ions are excited to emit radiation by the heat of plasma 17. Radiation emitted by excited atoms and ions can be used for spectrochemical analysis by optical emission spectrometry, as is known in the art. Furthermore, ions in central channel 18 can be used for analysis by mass spectrometry, as is also known in the art.

Figure 2:
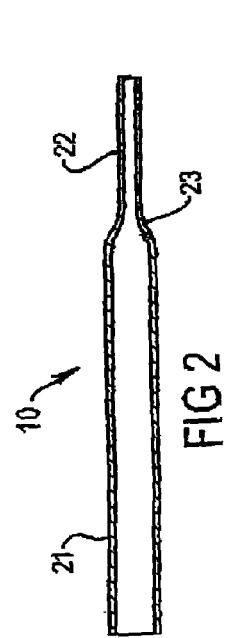

In order that aerosol emerging from outlet 35 of tube 10 may effectively penetrate plasma 17 and form central channel 18, it is known to provide a narrow parallel-walled path through at least a portion of tube 10 adjacent to its outlet 35, so that the flow therethrough is substantially laminar. In FIG. 1 such a narrow parallel-walled path is shown extending the entire length of tube 10. It is also known, however, that such a long, narrow passage or capillary is readily obstructed by salts deposited from the aerosol when aerosols generated from samples containing high levels of dissolved solids are introduced into tube 10. Accordingly, it is also known to provide a tube as shown in FIG. 2, which has a wide parallel-sided portion 21, extending for a substantial length of the tube from the end through which the aerosol enters, and a narrow, parallel-sided short portion 22, extending from the end through which the aerosol outlet ends. Portions 21 and 22 are joined by a short tapered portion 23. A tube 10 according to FIG. 2 is more resistant to blockage by deposited salts than is a tube 10 as shown in FIG. 1, in which the narrow parallel-side portion extends the entire length of tube 10. None the less, a torch equipped with a tube 10 according to FIG. 2 is still subject to obstruction by deposited salts. The deposition of salts is particularly evident in the short tapered portion 23.

Figure 3:
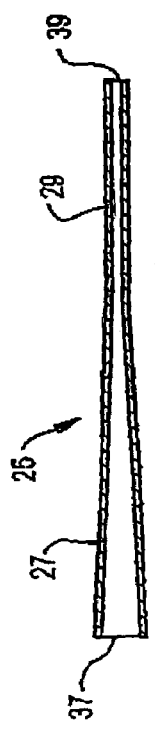

Having observed that salt deposited preferentially in the short tapered portion 23, the inventor decided to make the tapered portion as remote as possible from the heat of the plasma (to reduce the temperature of that portion) and also to make the transition of flow into the narrow parallel-walled portion as gradual as possible. This led to the design of a tube 25 as shown in FIG. 3, which has a tapered portion 27 of greatly increased length compared to section 23 of tube 10 of FIG. 2. The tube 25 is substantially constantly tapered along at least a substantial portion of its length such that its cross-sectional area gradually and smoothly reduces between is inlet 37 and its outlet 39 along said at least a substantial portion of its length Tube 25 includes a narrow parallel sided portion 29 similar to portion 22 of tube 10 of FIG. 2. It is probable, but not yet experimentally verified, that the tapered portion 27 could extend over the entire length of tube 25, the taper at the outlet end 39 approximating the narrow parallel-sided portion 29, such that the flow of sample aerosol laden gas within tube 25 at outlet 39 is substantially laminar.

FIG. 4 shows an embodiment of a tube 25 of the invention wherein aerosol is introduced into tube 25 through a smoothly curved tube 31 that is continuous with tapered portion 27. Curved tube 31 is advantageous for the particular spectrometer in which the invention was tested. In another spectrometer, for example one in which the torch is mounted vertically, curved tube 31 might not be required.

FIG. 5 shows an inductively coupled plasma torch 40 equipped with a central tube 25 according to the invention. Components of this torch that are the same as in torch 9 of FIG. 1 have been accorded the same reference numeral. Note that a torch 40 according to the invention in its broadest form involves provision of the three tubes 25, 11 and 13 without the radio frequency induction coil 16.

To assess the performance of the tube 25 of the invention, tests were carried out in which a solution containing 250 grams of sodium chloride per liter was nebulised continuously into either an operating prior art torch having a tube 10 according to FIG. 2 or into an operating torch having a tube 25 according to this invention (as in FIG. 4). The sample introduction system and the operating conditions of the inductively coupled plasma were the same in each of the tests and were typical of those that would be used in normal operation of an inductively coupled plasma atomic emission spectrometer. The prior art torch was blocked within 30 minutes, but the torch 40 according to the invention was still operational after 24 hours. Observation of the blocking process revealed that salt built up continuously in the prior art torch, leading to blockage. In the torch according to the invention, salt was deposited in the curved portion 31 and in the wide part of the tapering portion 27 of tube 25 just after curved portion 31. This deposited salt was in the form of a fine granular material, some of which was from time to time blown right through tube 25 and into central channel 18. A torch according to the invention is thus to some extent self-clearing. It is emphasised that continuous introduction of sample is a very severe test. In real analytical practice, the system would be rinsed between samples by aspirating a blank solution and this would prolong the useful analytical time considerably.

Example dimensions for a tube 25 are: length approximately 90 mm, inlet diameter 5 mm, outlet diameter 2.3 mm, length of tapered portion approximately 40 mm extending to approximately 45 mm from the outlet.

Further test results are illustrated in FIG. 6 which shows a plot of reported test element concentration versus time for a solution containing 1 milligram of each of three test elements (barium, zinc and magnesium) and 250 grams of sodium chloride per liter of solution. The solution was introduced continuously into an inductively coupled plasma sustained in a torch having a tube 25 (as in FIG. 4) according to the invention while the concentration of each test element was monitored on the basis of the measured intensity of the emission lines indicated in the Figure (that is, Ba 455.403 nm, Zn 206.200 nm, Mg 280.270 nm, Mg 285.213 nm).

These results show that the torch was operating satisfactorily after 24 hours' continuous operation.

Figure 7:
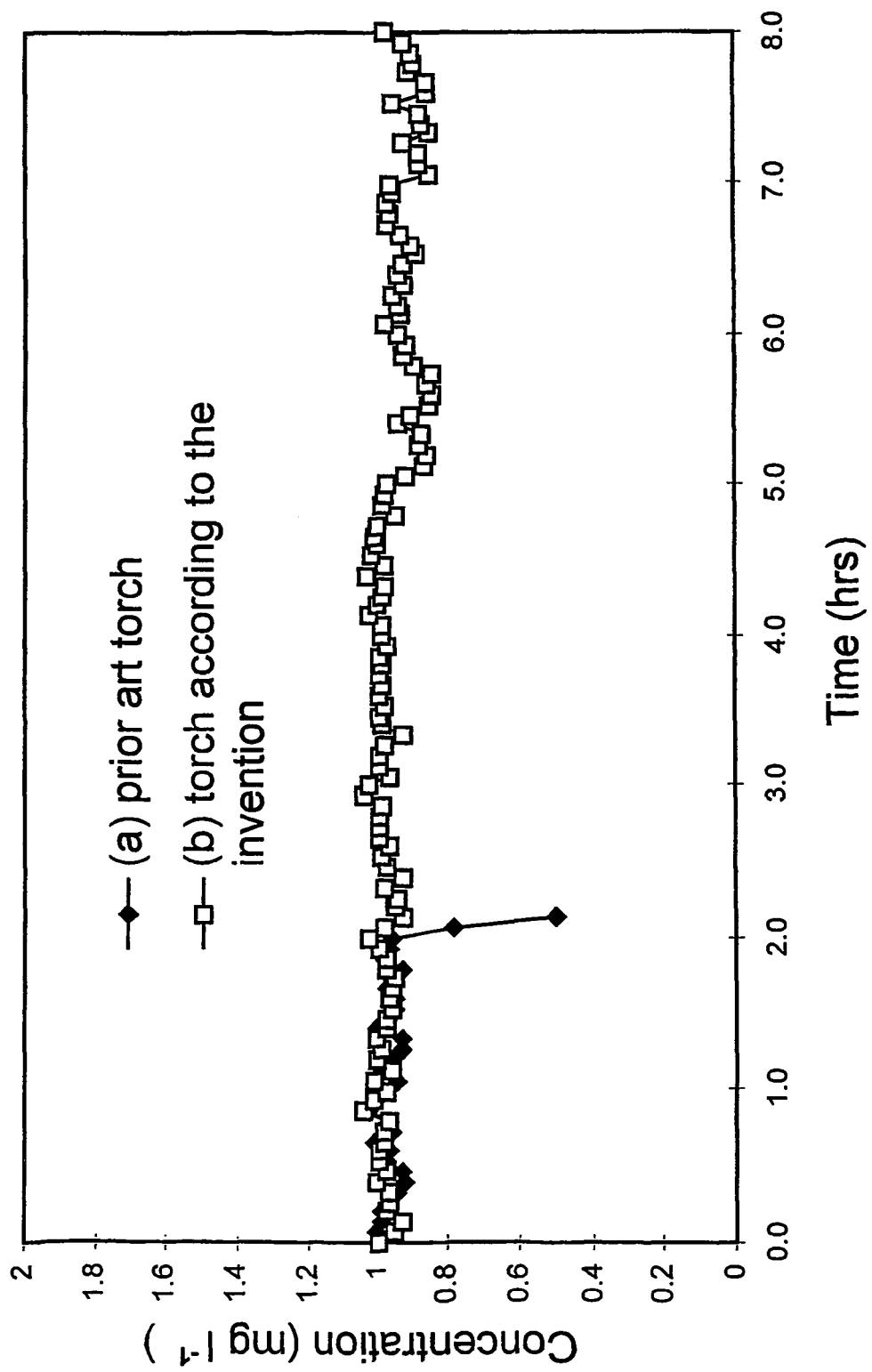

FIG. 7 shows a plot of reported manganese concentration versus time for a solution containing one milligram of manganese and 250 grams of sodium chloride per liter of solution. The solution was introduced continuously into an inductively coupled plasma sustained (a) in a prior art torch and then (b) in a torch having a tube 25 (as in FIG. 4) according to the invention while the concentration of manganese was monitored on the basis of the measured intensity of the 257.610 nm emission line. The same sample introduction system was used with each torch. The prior art torch blocked after two hours, but the torch according to the invention was still operating satisfactorily after 8 hours' continuous operation.

Table 1 shows the detection limit for a range of elements in dilute nitric acid solution (a) in a prior art torch and (b) in a torch according to the invention. This solution is easily handled by the prior art torch, yielding state-of-the-art detection limits. Similar detection limits were obtained with the torch according to the invention.

TABLE 1

| | | Detection Limit, micrograms/liter | |
| --- | --- | --- | --- |
| Element | Wavelength (nm) | (a) prior art torch | (b) torch according to the invention |
| Al | 167.019 | 0.30 | 0.40 |
| As | 188.980 | 3.4 | 3.6 |
| Ba | 455.403 | 0.12 | 0.13 |
| Be | 234.861 | 0.05 | 0.05 |
| Ca | 396.847 | 0.03 | 0.03 |
| Cd | 214.439 | 0.17 | 0.14 |
| Cu | 327.396 | 0.67 | 0.64 |
| Fe | 238.204 | 0.24 | 0.29 |
| Mg | 279.553 | 0.016 | 0.013 |
| Mn | 257.610 | 0.05 | 0.057 |
| Mo | 202.032 | 0.58 | 0.56 |
| Ni | 231.604 | 0.88 | 1.0 |
| Pb | 220.353 | 2.0 | 2.3 |
| Se | 196.026 | 4.9 | 6.4 |
| Zn | 213.857 | 0.14 | 0.15 |

Figure 6:
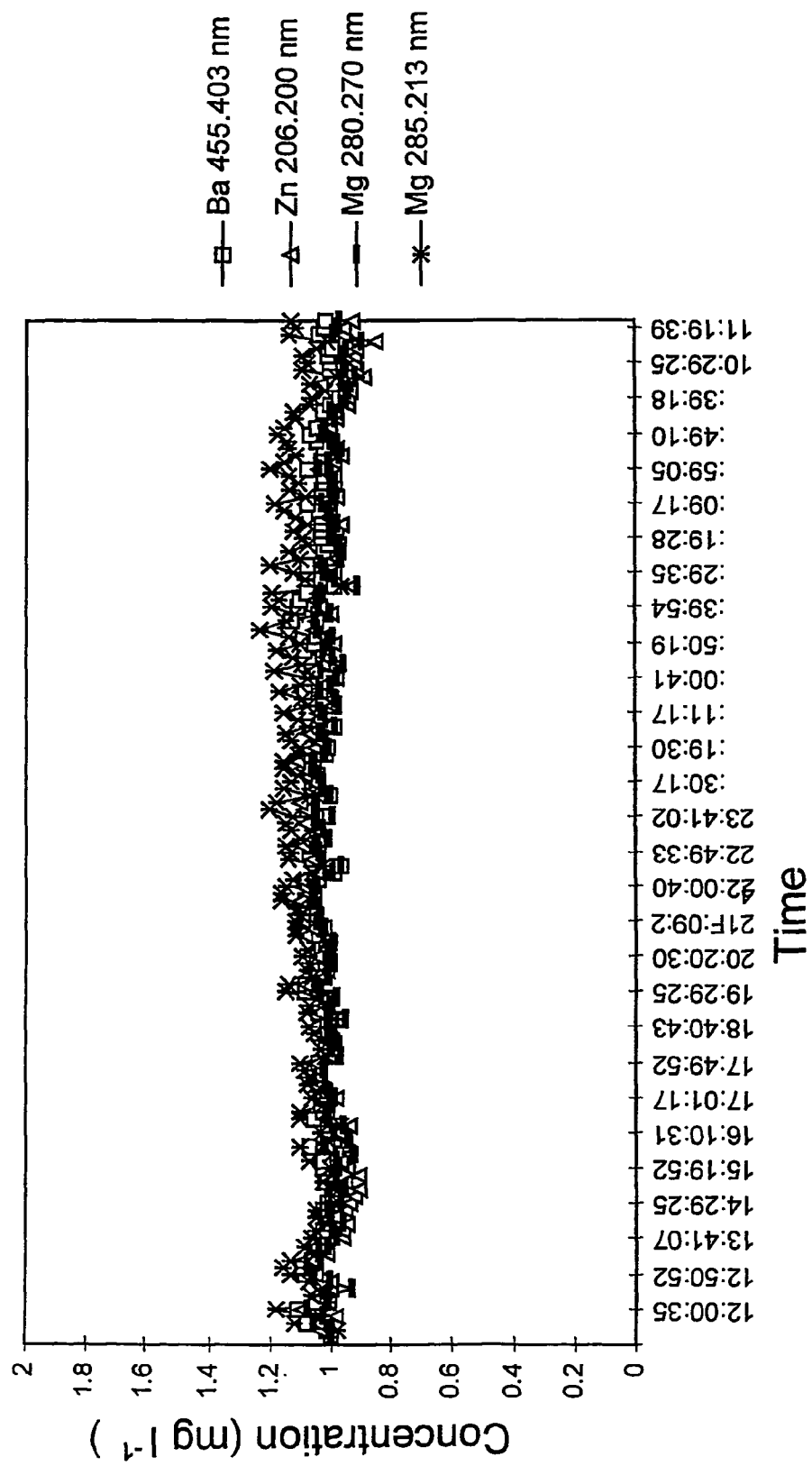

Table 2 shows the detection limit for a range of elements in a solution of 250 grams of sodium chloride per liter in dilute nitric acid, measured with a torch according to the invention. This solution rapidly blocks the prior-art torch (FIG. 7), but a torch according to the invention yields stable signals for prolonged periods (FIG. 6) and also provides satisfactorily low detection limits.

TABLE 2

| Element | Wavelength (nm) | Detection Limit, micrograms/liter |
| --- | --- | --- |
| Al | 167.019 | 1.5 |
| As | 188.980 | 7.5 |
| Ba | 455.403 | 0.40 |
| Be | 234.861 | 0.30 |
| Ca | 396.847 | 0.20 |
| Cd | 214.439 | 0.90 |
| Co | 238.892 | 2.0 |
| Cr | 267.716 | 1.0 |
| Cu | 327.396 | 3.0 |
| Fe | 259.94 | 6.0 |
| Mg | 279.553 | 0.20 |
| Mn | 257.610 | 0.20 |
| Pb | 220.353 | 11 |

TABLE 2-continued

| Element | Wavelength (nm) | Detection Limit, micrograms/liter |
| --- | --- | --- |
| Ti | 334.941 | 0.90 |
| V | 292.401 | 1.5 |
| Zn | 213.857 | 1.0 |

The discussion herein of the background to the invention and what is known is included to explain the context of the invention. This is not to be taken as an admission that any of the matters referred to were part of the common general knowledge in Australia as at the priority date of this application.

The invention described herein is susceptible to variations, modifications and/or additions other than those specifically described and it is to be understood that the invention includes all such variations, modifications and/or additions that fall within the scope of the following claims.

The invention claimed is:

1. A torch for producing a plasma for use in spectrochemical analysis comprising:
   a tube for conveying a flow of a gas carrying sample aerosol to a plasma produced in the torch by an electromagnetic field, the tube having an inlet and an outlet of smaller size than the inlet, and being shaped to deliver a substantially laminar flow of the gas at the outlet, wherein the tube is tapered along its length for a distance that is at least five times the internal diameter of the inlet of the tube such that its cross-sectional area gradually and smoothly reduces towards its outlet along at least such portion of its length.

2. A torch as claimed in claim 1, wherein the tube is tapered along its length for a distance that is from five to ten times the internal diameter of the inlet of the tube.

3. A torch as claimed in claim 1, wherein the tube comprises a parallel walled portion extending to the outlet, wherein the tapered portion of the tube smoothly blends into the parallel walled portion.

4. A torch as claimed in claim 1, wherein the tapered portion of the tube commences at the inlet.

5. A torch as claimed in claim 1, wherein the tube is tapered along substantially is whole length.

6. A torch as claimed in claim 1, wherein the tube comprises:
   an inlet portion that is smoothly curved through an angle of about 90° and smoothly bends into the tapered portion.

7. A torch as claimed in claim 1, wherein the taper of the tapered portion of the tube is constant.

8. A torch as claimed in claim 1, wherein the tube is concentrically located within a second tube and the second tube is concentrically located within a third tube, the third tube including an inlet for supplying a flow of a plasma forming gas to the annular outlet formed between the second and third tubes, the second tube also including inlet for supplying a flow of gas to the annular outlet formed between the first defined tube and the second tube for keeping a plasma away from the outlet ends of the first defined tube the second tube.

* * * * *